United States Patent [19]

Farris et al.

[11] Patent Number: 4,492,577
[45] Date of Patent: Jan. 8, 1985

[54] SURGICAL IMPLANTS WITH SOLID INTERIORS AND POROUS SURFACES

[76] Inventors: Edward T. Farris, 4715 Greenville Ave., Dallas, Tex. 75206; J. Lester Matthews, 6944 Lakewood Blvd., Dallas, Tex. 75214

[21] Appl. No.: 436,618

[22] Filed: Oct. 25, 1982

[51] Int. Cl.³ .............................................. A61C 8/00
[52] U.S. Cl. .................................... 433/201; 433/173
[58] Field of Search ............... 433/173, 174, 175, 176, 433/201, 220, 221; 3/1.9, 1.91, 1.911, 1.912, 1.913; 128/92 C; 264/255; 427/2, 133

[56] References Cited

U.S. PATENT DOCUMENTS

| | | | |
|---|---|---|---|
| 2,357,950 | 9/1944 | Goessling | 264/255 |
| 3,745,590 | 7/1973 | Stubstad | 3/1 |
| 3,826,241 | 7/1974 | Bucalo | 433/173 |
| 3,863,344 | 2/1975 | Pillet | 433/173 |
| 3,906,550 | 9/1975 | Rostoker et al. | 433/201 |
| 3,934,347 | 1/1976 | Lash et al. | 128/92 C |
| 3,971,134 | 7/1976 | Bokros | 433/201 |
| 4,064,567 | 12/1977 | Burstein et al. | 3/1.91 |
| 4,146,936 | 4/1979 | Aoyagi et al. | 427/2 |
| 4,252,525 | 2/1981 | Child | 433/201 |
| 4,261,063 | 4/1981 | Blanquaert | 3/1.91 |

OTHER PUBLICATIONS

M. B. Weiss et al., "Development of a New Endosseus Dental Implant. Part I: Animal Studies", *J. Prosthetic Dentistry*, 46#6: 646-651, (1981).

*Primary Examiner*—John J. Wilson
*Attorney, Agent, or Firm*—Hamilton, Brook, Smith and Reynolds

[57] ABSTRACT

A device is disclosed which has a solid interior and at least one surface which is porous. The porous surface has several desired characteristics, including: (1) the majority of pores have dimensions within a size range that encourages the migration of cells into said pores, such as about 50 to about 500 micron diameters, and (2) the pores have a controlled depth, such as about 300 microns or less. Such devices may be created by several methods, such as injecting casting material into a mold which is fitted with a shell of porous material having the desired shape and characteristics. Such devices are useful as artificial teeth and orthopedic appliances.

4 Claims, 2 Drawing Figures

SURGICAL IMPLANTS WITH SOLID INTERIORS AND POROUS SURFACES

DESCRIPTION

1. Technical Field

This invention is in the fields of prosthetic devices and metallurgy.

2. Background Art

Various types of tissue are capable of generating a stronger attachment to surgical implants having a porous surface than to implants having only smooth surfaces. This is due to a variety of factors, including increased surface area and cellular migration into the pores of the implant, which creates a matrix of tissue that is intertwined with the material of the porous implant.

Various types of artificial teeth and other surgical implants have been developed which have porous surfaces. However, surgical implants made of porous material alone may not be sufficiently strong for certain types of uses, such as implants for artificial teeth or implants requiring attachment to bone or other devices. Therefore, it may be necessary to emplace a piece of solid material, such as a metallic center post, within the interior of a surgical implant having a porous shell or surface. See, for example, M. B. Weiss et al, "Development of a New Endosseus Dental Implant. Part I: Animal Studies," *Journal of Prosthetic Dentistry, Vol.* 46 #6: 646–651 (1981).

For devices having regular shapes such as cylinders, it may be possible to create the porous outer structure and the solid inner piece separately, then assemble the pieces. However, for various other shapes, such as replicas of tooth root (particularly multi-rooted shapes), this type of assembly may not be possible. For such irregularly-shaped implants, it may be necessary to create such implants by alternate means.

One potential method for creating such devices comprises a technique commonly referred to as the "lost wax" method. This method may be briefly summarized as follows: a "pattern" of the device is created in wax, plastic or other material. The pattern is attached to a "sprue" which creates a support for the pattern. The pattern and sprue are then surrounded by material which is called an "investment." This may be accomplished by various means, such as spreading paste or other investment material on the surface of the pattern and sprue, or by immersing the pattern and sprue in investment material. The sprue extends to the surface of the investment, creating a channel for the subsequent flow of material.

The wax, plastic, or other material which forms the pattern and sprue is then removed, leaving behind the investment material having a vacancy with a desired shape created by the pattern. The pattern and sprue may be removed by several methods, depending upon the material utilized. For example, if wax is utilized, the investment and pattern may be heated, causing the wax to melt and drain out of the investment material via the channel formed by the sprue. The investment material is then utilized as a mold.

When the mold is at the proper temperature, the material to be cast is introduced as a liquid (generally molten metal) into the mold. Centrifugation, high pressure, and other techniques may be utilized if desired to ensure that the liquid fills all of the spaces within the mold that were previously occupied by the wax of the pattern, sprues, etc. This liquid is allowed to cool, causing it to solidify. The investment material is then removed, and the sprue is then separated from the casting. The casting may be machined and polished if desired to produce the final configuration or surface quality.

A different casting method, which may be referred to as the split mold method, is commonly used. This method involves a mold, made of ceramic or other material, which is divided into two or more parts. Each mold part has a flat or curvilinear surface with one or more shaped depressions. When the mold parts are held together, the shaped depressions create a vacant space into which casting material is injected. After the cast material hardens, the mold parts may be separated, allowing the cast item to be removed. The mold parts normally may be reused numerous times.

However, casting methods are not sufficiently precise to create surgical implants having solid interiors and having optimal surface porosity. For example, it would be very difficult to create an implant having surface pores which are uniformly within a size range which encourages the growth of cells into the pores, such as about 50 to about 500 microns, and which extend an optimal distance into the surface of the implant.

DISCLOSURE OF INVENTION

This invention relates to a device that is suitable for surgical implantation. The device has at least one solid piece, at least one surface of which is covered by one or more layers of porous material having several desired characteristics. Such characteristics include the following:

a. controlled pore diameters which are within a size range that encourages the migration of cells into said pores;

b. controlled pore depths which are sufficiently deep to allow and encourage firm attachment of the device to surrounding tissue, yet not so deep that adverse effects are created;

c. all exposed surfaces should be made of a biocompatible material;

d. the edges that define the pore margins should not cut or otherwise injure cells or tissue that grows into the pores;

e. the porous material should be sufficiently strong to withstand all stresses that are likely to be imposed on the device;

f. the porous material should not be damaged by the conditions used to create the device; and, g. the porous material should be attached to the solid material with sufficient strength to prevent detachment.

Such devices may be created by several methods, including injecting casting material, in molten or other fluidized form, into a mold which is fitted with porous material having the desired shape and characteristics. Such molds may be created by a variety of methods, several of which are described below.

The devices of this invention have a combination of desired characteristics which render them very useful as artificial teeth and orthopedic implants. Such devices may also be coated with biocompatible materials such as hydroxyapatite to increase their usefulness as surgical implants.

BEST MODE OF CARRYING OUT THE INVENTION

Figure 1:
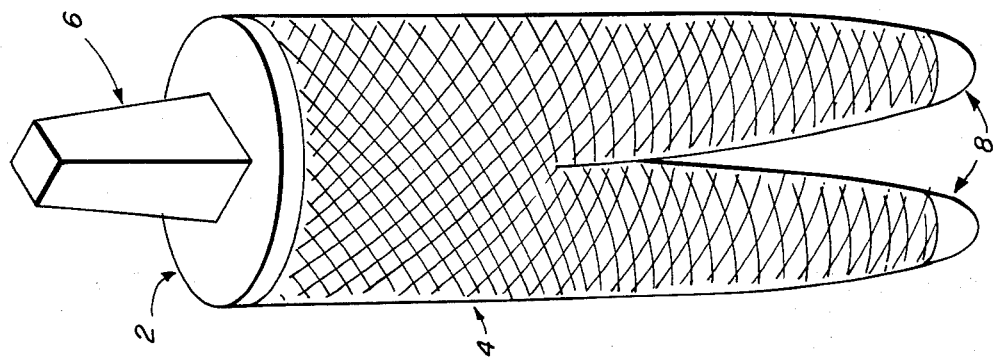
FIG. 1 is a drawing of an artificial tooth with a solid interior and a root structure with a porous surface.

One preferred embodiment of this invention comprises a device that is suitable for implantation as an artificial tooth, as shown in FIG. 1. One or more surfaces of a solid piece 2 are surrounded by porous material 4. Protrusion 6 serves as an attachment post for various devices, such as a crown made of ceramic, metal or other material. Protrusion 8 serves as the tip of the tooth root, which preferably has a smooth rather than a porous surface.

One preferred method for creating this device is as follows. A hollow shell having a desired shape is created from a cylinder of porous material. Cylinders of porous metal are commercially available; see, e.g., the product catalog of the Filter Products Division of Facet Enterprises, Inc. (Madison Heights, MI). Such cylinders may be created from any material which is sufficiently ductile to be drawn into fine wire. Several metals which are relatively biocompatible, such as ASTM 316-SS, surgical stainless steel, and Surgical Vitallium (Howmedica Co., Chicago, Ill.) may be utilized.

The fine wire may be flattened, if desired, into very small ribbons. The wires or ribbons may be woven into a single-layered cylinder using a mandrel for support. If desired, any number of layers may be woven around the mandrel, to create a cylinder with any desired thickness. A significant aspect of this invention is that the depth of the pores may be carefully controlled by controlling the thickness of the porous cylinder. This is important for several reasons, including the following. First, most cells cannot function properly if they are more than a certain distance from the nearest blood vessel; for most types of cells, this distance is about 300 microns. If the pores of an implant are too narrow to allow for vascularization, and yet greater than about 300 microns deep, they may become filled with inert body fluids or dead cells, either of which may be undesirable. Second, it may be desired to coat the porous surface of the device with hydroxyapatite or other materials in order to increase the biocompatibility of the device and to encourage cell migration into the pores of the device. However, it is difficult to coat all of the surfaces of a pore which is narrow and very deep. By controlling the depth of the pores, devices may be created which are more suitable for coating.

If desired, the mandrel used to create the cylinder may be tapered to create a conical shell. Cylinders of any desired diameter and length may be created. By varying the size and weaving density of the wires or ribbons, it is possible to control the pore size of the material; it is believed that an average pore dimension of about 50 to about 500 microns is preferable. The term "dimension" may refer to a diameter if the pore is circular, or to a diagonal or side if the pore is polygonal.

A significant advantage arises from utilizing woven porous material rather than porous material created by compaction, sintering, or other such methods. Porous devices created by compaction, sintering, and other techniques tend to have pores with a broad range of pore sizes, including pores that are too small and pores that are too large to encourage cell migration into the pores. By contrast, woven material can be created wherein the large majority of pores are within the desired size range. Cells are likely to migrate into a much larger number of pores in woven material than in compacted or sintered material, thereby creating a firmer attachment of the device to the surrounding tissues.

If desired, a porous cylinder may be created out of layers having different pore sizes, or from layers made from different material. For example, the innermost layer of the cylinder may be made of a material which will resist heat or provide a strong bond to the solid cast material, while the outermost layer may be made of material with greater biocompatibility.

The cylinder of porous material may be shaped into the desired configuration by means known to those skilled in the art, using tools such as jigs, pliers, and crimping devices. A porous shell having a complex shape such as a tooth with two or three roots may be created by various means, such as using multiple cylinders, by crimping one end of a large cylinder or by using a combination of porous devices such as cylinders and flat pieces.

When the porous shell is completed, it may be fitted into one part of a split mold. The mold is then closed around the shell.

In an alternate method of this invention, a porous shell is created having a desired configuration. A pattern is then created by inserting wax, plastic or other material into the porous shell. The pattern material is then shaped into the desired configuration, which normally will include a sprue, by conventional means. The pattern and porous shell are then surrounded by investment material. The pattern and sprue are then removed by heat or other means. Alternately, if the pattern material comprises rubber or other elastomeric material, it may be removed from the mold by tension.

Figure 2:
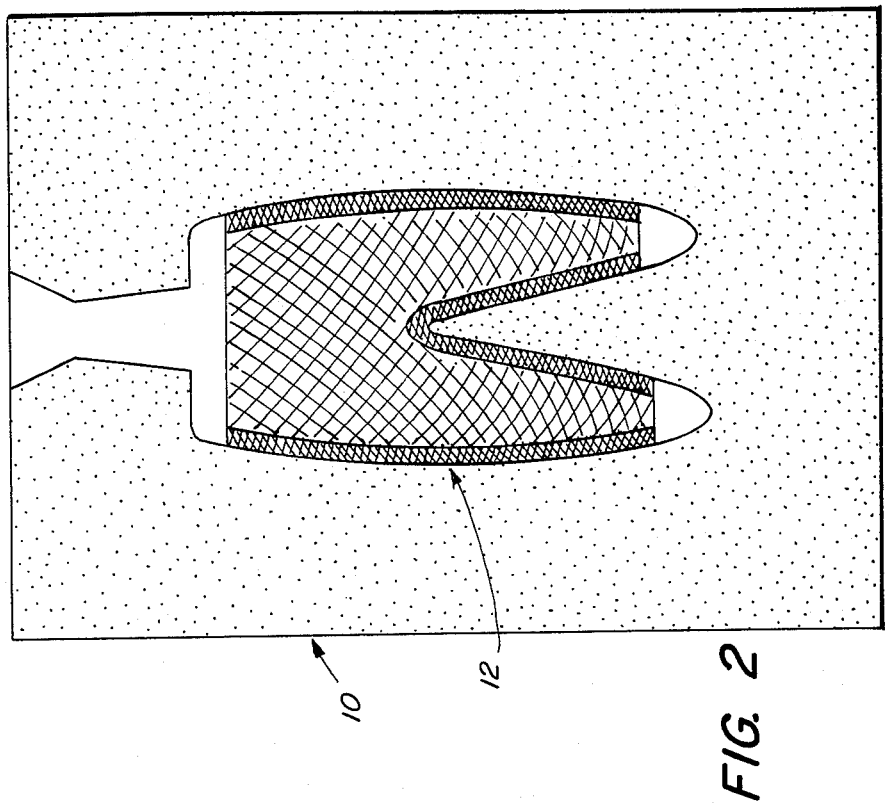
FIG. 2 is a cross-sectional drawing of a mold containing a shell of porous material.

All of the foregoing methods will create a Mold 10 which contains a porous Shell 12, as shown in FIG. 2. Casting material is injected into the mold and allowed to harden. The mold is then removed from the casting. If the proper casting material and injection conditions are used, a small quantity of casting material will permeate into one or more of the inner layers of the porous shell. When the cast material hardens, this creates a relatively strong attachment between the solid cast material and the porous material, without destroying the porosity of the outer layers of the porous material.

The completed device, produced by any one or combination of methods described above, may be cleaned of any remaining substance adherant thereto which is not of the original porous shell and the material cast into its mold. After cleaning, any sprues or flashings may be removed from the casting and the implant may be refined by machining or polishing as desired. Additional cleaning of the implant may be performed by various methods such as ultrasonic agitation, to insure that all contaminants are removed from the device. The device is then ready for further treatment, such as sterilization, additional fittings, chemical or physical treatment of the surface or body or parts thereof, electromechanical treatment or other processes or combination of processes, assembly of parts, and packaging.

As used herein, the term "biocompatible" refers to a substance or device which has characteristics that eliminate or minimize adverse reactions when the substance or device is implanted in a body. Such materials should not cause antigenic, pyogenic, pyrogenic or inflammatory responses in the recipient. They should not cause galvanic currents, or be corroded, metabolized or dissolved into undesired substances.

Devices of this invention may be created by a variety of means other than casting. For example, it is possible to create surface porosity by attaching one or more layers of porous material to a solid surface. Attachment may be accomplished by several means, such as welding, sintering, or cementing depending upon a variety of factors such as the composition and structure of the porous and solid materials.

Alternately, it is possible to create surface porosity by removing material from the surface of a solid device, using techniques such as etching by means of acid, laser radiation, or electron bombardment.

Those skilled in the art will recognize or be able to ascertain using no more than routine experimentation, numerous other techniques which may be utilized to create the device of this invention. Such devices are within the scope of the following claims.

We claim:

1. A device for surgical implantation comprising a solid metallic core piece surrounded by a porous shell formed of a woven, metal material bonded firmly to said core piece, the pores of the shell having a depth of about 300 microns or less and a diameter or a diagonal of about 50 to about 500 microns.

2. A device of claim 1 wherein the porous shell surrounds part of the core piece to provide a smooth surface.

3. A device of claim 1 wherein said woven, metal material is biocompatible.

4. A device of claim 1, produced by injecting a molten metal casting material into a mold lined with a biocompatible woven, metal material under conditions which cause the casting material to enter the pores of the woven metal material but not permeate the entire thickness of the pores, such that the core piece extends partway into the pores of the woven metal material which forms the shell, thereby providing a pore depth of less than 300 microns.

* * * * *